US011705228B2

(12) United States Patent
Ishikawa

(10) Patent No.: US 11,705,228 B2
(45) Date of Patent: Jul. 18, 2023

(54) CONTROL OF VIEWING OF PATIENT INFORMATION SHARED BETWEEN HEALTHCARE FACILITIES

(71) Applicant: Konica Minolta Healthcare Americas, Inc., Wayne, NJ (US)

(72) Inventor: Takayuki Ishikawa, Wayne, NJ (US)

(73) Assignee: Konica Minolta Healthcare Americas, Inc., Wayne, NJ (US)

( * ) Notice: Subject to any disclaimer, the term of this patent is extended or adjusted under 35 U.S.C. 154(b) by 111 days.

(21) Appl. No.: 16/987,847

(22) Filed: Aug. 7, 2020

(65) Prior Publication Data

US 2022/0044770 A1 Feb. 10, 2022

(51) Int. Cl.
   *G16H 10/60* (2018.01)
   *G16H 40/67* (2018.01)
(52) U.S. Cl.
   CPC ............. *G16H 10/60* (2018.01); *G16H 40/67* (2018.01)
(58) Field of Classification Search
   CPC ................................ G16H 10/60; G16H 40/67
   See application file for complete search history.

(56) References Cited

U.S. PATENT DOCUMENTS

2018/0218074 A1\* 8/2018 Ishikawa ................ G16H 10/60
2018/0234497 A1\* 8/2018 Ueda .................... H04L 67/1097

FOREIGN PATENT DOCUMENTS

JP          2005025357 A  \*  1/2005
JP          2008-59176 A      3/2008

\* cited by examiner

*Primary Examiner* — Michael Tomaszewski
*Assistant Examiner* — Mohmad Muqueeth
(74) *Attorney, Agent, or Firm* — Osha Bergman Watanabe & Burton LLP

(57) ABSTRACT

A method for managing patient information in a system includes a cloud server, a healthcare facility, and affiliated facilities connected via a network. The method includes: receiving, from the healthcare facility, a medical image in response to examination order information sent by a first user from one affiliated facility; correlating the medical image to the examination order information and adding them to the patient information; correlating the medical image to disclosure propriety information indicating whether to allow the patient information to be disclosed to a second user; receiving a viewing request sent by the first or second user from one affiliated facility; determining whether to approve the viewing request based on the examination order information or the disclosure propriety information; and approving the viewing request and transmitting the patient information to the affiliated facility from which the viewing request has been sent.

15 Claims, 7 Drawing Sheets

FIG. 2

| EXAM ID | PATIENT ID | IMAGE DATA |
|---|---|---|
| 111 | Patient1 | DICOM1 |
| 222 | Patient2 | DICOM2 |
| 333 | Patient3 | DICOM3 |
| ... | ... | |

FIG. 3

| EXAM ID | ORDER ID | EXAMINED PORTION | DOCTOR/RADIOLOGIST |
|---|---|---|---|
| 111 | Order1 | LEG PART | Doctor X |
| 222 | Order2 | HEAD | Radiologist Y |
| 333 | Order3 | CHEST | Doctor Z |
| ... | ... | ... | ... |

FIG. 4

| PATIENT ID | FLAG | PATIENT NAME | GENDER | DOB |
|---|---|---|---|---|
| Patient1 | 1 | Bob | M | 1980/1/1 |
| Patient2 | 2 | Mary | F | 2010/4/1 |
| Patient3 | 3 | John | M | 1995/6/30 |
| ... | ... | ... | ... | ... |

FIG. 5

| FLAG | STATUS |
|---|---|
| 1 | DENY |
| 2 | APPROVE |
| 3 | CONDITIONALLY APPROVE(*) |

* PERMIT TO FACILITY/DOCTOR THAT EXAMINES SUBJECT PATIENT

CONTROL OF VIEWING OF PATIENT INFORMATION SHARED BETWEEN HEALTHCARE FACILITIES

BACKGROUND

Medical images and medical data play a crucial role in the diagnosis of a patient. Healthcare facilities (e.g., hospitals) have realized the benefits of electronically storing medical images and medical data. The digitalization of the medical images and data ("medical data") not only enables healthcare professionals to easily access medical images and medical data, but also enables the images and data to be easily shared between multiple facilities through the use of physical mediums such as compact discs (CDs), digital video discs (DVDs), and Universal Serial Bus (USB) flash drives.

More recently, cloud-based storage systems have emerged as a way to improve efficiency and accessibility of information. In general, a "cloud" is an online storage system that provides remote, on-demand access of computing resources and data over the Internet to multiple computers and devices in various locations. Cloud-based storage may be provided by vendors who use remote or off-site data centers in various locations for storage of data such as medical images. The vendors of the cloud-based storage may also provide a common viewing system ("a universal viewer") that allows the facilities to retrieve a complete set of the patient's medical data taken or stored at other facilities through a single request.

However, because the cloud-based storage generally saves medical images including a plurality of regions of a patient's body (e.g., head, chest, abdomen, pelvic part, and leg part) acquired by one examination, a user (e.g., doctor) of the universal viewer must search for medical images of certain region(s) of interest (e.g., regions belonging to the user's field of specialty).

To allow each user to more easily obtain specific medical information (e.g., medical images) of his or her interest, a network system may comprise an image server that provides medical images of predetermined regions to each of the facilities. With such a system, however, a user would be authorized to view only the medical images of the region(s) captured in response to the user's request, and would be unable to view other medical images.

SUMMARY

One or more embodiments provide a method for managing a plurality of pieces of patient information in a system that shares the patient information among a cloud server comprising a storage, a healthcare facility comprising an imaging device, and affiliated facilities, wherein the cloud server, the healthcare facility, the affiliated facilities are connected to one another via a network, the method comprising: receiving, from the healthcare facility, a medical image created by the imaging device in response to examination order information sent by a first user from one of the affiliated facilities; correlating the received medical image to the examination order information and adding the medical image and the examination order information to the patient information stored in the storage; correlating the medical image to disclosure propriety information in the storage, wherein the disclosure propriety information indicates whether to allow the patient information to be disclosed to a second user; receiving a viewing request sent by the first user or the second user from one of the affiliated facilities to view the patient information; determining whether to approve the viewing request based on the examination order information or the disclosure propriety information; and approving the viewing request for the first user or the second user to view the patient information and transmitting the patient information to the one of the affiliated facilities from which the viewing request has been sent.

One or more embodiments provide a non-transitory computer-readable medium (CRM) storing an instruction that causes a cloud server to perform an operation for managing a plurality of pieces of patient information in a system that shares the patient information among a cloud server comprising a storage, a healthcare facility comprising an imaging device, and affiliated facilities, wherein the cloud server, the healthcare facility, and the affiliated facilities are connected to one another via a network, the operation comprising causing the cloud server to: receive, from the healthcare facility, a medical image created by the imaging device in response to examination order information sent by a first user from one of the affiliated facilities; correlate the received medical image to the examination order information and add the medical image and the examination order information to the patient information stored in the storage; correlate the medical image to disclosure propriety information in the storage, wherein the disclosure propriety information indicates whether to allow the patient information to be disclosed to a second user; receive a viewing request sent by the first user or the second user from one of the affiliated facilities to view the patient information; determine whether to approve the viewing request based on the examination order information or the disclosure propriety information; and approve the viewing request for the first user or the second user to view the patient information and transmit the patient information to the one of the affiliated facilities from which the viewing request has been sent.

One or more embodiments provide a system that manages a plurality of pieces of patient information, comprising: a cloud server that comprises a storage; a healthcare facility that comprises an imaging device; and affiliated facilities, wherein the system shares the patient information among the cloud server, the healthcare facility, and the affiliated facilities via a network, and the cloud server: receives, from the healthcare facility, a medical image created by the imaging device in response to examination order information sent by a first user from one of the affiliated facilities; correlates the received medical image to the examination order information and adds the medical image and the examination order information to the patient information stored in the storage; correlates the medical image to disclosure propriety information in the storage, wherein the disclosure propriety information indicates whether to allow the patient information to be disclosed to a second user; receives a viewing request sent by the first user or the second user from one of the affiliated facilities to view the patient information; determines whether to approve the viewing request based on the examination order information or the disclosure propriety information; and approves the viewing request for the first user or the second user to view the patient information and transmits the patient information to the one of the affiliated facilities from which the viewing request has been sent.

Other aspects and advantages of the invention will be apparent from the following description and the appended claims.

BRIEF DESCRIPTION OF DRAWINGS

FIG. 2 shows a table of a database stored in a cloud server according to one or more embodiments.

FIG. 3 shows another table of the database stored in a cloud server according to one or more embodiments.

FIG. 4 shows another table of the database stored in a cloud server according to one or more embodiments.

FIG. 5 shows another table of the database stored in a cloud server according to one or more embodiments.

DETAILED DESCRIPTION

Figure 1:
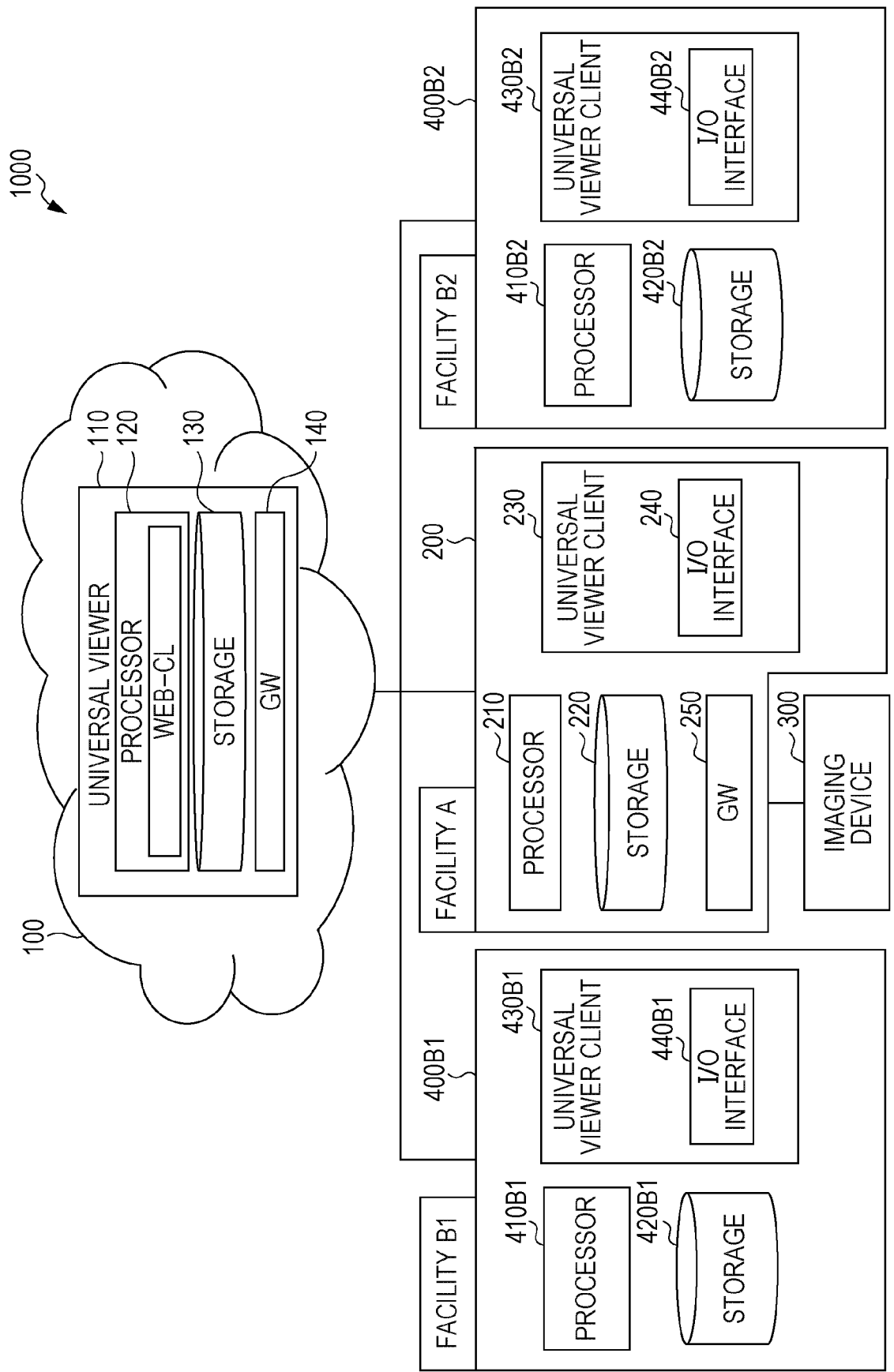
FIG. 1 shows a system according to one or more embodiments.

Specific embodiments will now be described in detail with reference to the accompanying figures. Like elements in the various figures are denoted by like reference numerals for consistency. Like elements may not be labeled in all figures for the sake of simplicity.

In the following detailed description of embodiments of the disclosure, numerous specific details are set forth in order to provide a more thorough understanding of the disclosure. However, it will be apparent to one of ordinary skill in the art that the disclosure may be practiced without these specific details. In other instances, well-known features have not been described in detail to avoid unnecessarily complicating the description.

Throughout the application, ordinal numbers (e.g., first, second, third, etc.) may be used as an adjective for an element (i.e., any noun in the application). The use of ordinal numbers does not imply or create a particular ordering of the elements or limit any element to being only a single element unless expressly disclosed, such as by the use of the terms "before," "after," "single," and other such terminology. Rather, the use of ordinal numbers is to distinguish between the elements. By way of an example, a first element is distinct from a second element, and the first element may encompass more than one element and succeed (or precede) the second element in an ordering of elements.

It is to be understood that the singular forms "a," "an," and "the" include plural referents unless the context clearly dictates otherwise. Thus, for example, reference to "a horizontal beam" includes reference to one or more of such beams.

Terms such as "approximately," "substantially," etc., mean that the recited characteristic, parameter, or value need not be achieved exactly, but that deviations or variations, including for example, tolerances, measurement error, measurement accuracy limitations and other factors known to those of skill in the art, may occur in amounts that do not preclude the effect the characteristic was intended to provide.

Although multiple dependent claims are not introduced, it would be apparent to one of ordinary skill that the subject matter of the dependent claims of one or more embodiments may be combined with other dependent claims.

[System Overview]

In general, one or more embodiments of the invention provide a method, a non-transitory computer readable medium, and a system that control viewing of patient information (e.g., medical images) across multiple healthcare facilities. The patient information may be obtained from examination (e.g., computerized tomography (CT), magnetic resonance imaging (MRI), etc.) conducted at one healthcare facility and shared across a plurality of affiliated facilities via a server (e.g., a cloud server). More specifically, one or more embodiments not only permit a user who requested the examination (i.e., a "first user") to view the patient information, but also permit another user, either at the same facility as the first user or at a different facility, to view the patient information under prescribed conditions (i.e., a "second user"). This enhances convenience for viewing the patient information in a universal viewer system without compromising security of the patient information. A "user" at a facility may be any healthcare professional such as a doctor, nurse, medical staff, medical technician, etc.

For example, a system according to one or more embodiments comprises (i) at least one healthcare facility comprising an imaging device (hereinafter "the healthcare facility") and (ii) multiple other affiliated facilities (each of which may or may not be a healthcare facility but will generally be referred to herein as "affiliated facility"). A user (first user) at one of the affiliated facilities sends a request for the examination to the healthcare facility to obtain the patient information of a certain patient. In response, the healthcare facility captures medical images of the patient and returns the medical images including metadata to the first user at the affiliated facility. At the same time, a cloud server obtains the patient information, including the medical images of the patient, from the healthcare facility. Thereafter, the cloud server provides the affiliated facilities with the patient information in response to a viewing request by the first user or another user (second user) from any one of the affiliated facilities under prescribed conditions.

According to one or more embodiments, each of the healthcare and affiliated facilities may be associated with one of a cloud-based storage system, a Picture Archiving and Communication System (PACS), or a cloud-based PACS provided by the same vendor or a different vendor.

According to one or more embodiments, the medical images and medical data may be stored in a Digital Imaging and Communications in Medicine (DICOM) format image. The medical images may also include multiple (e.g., tens to several hundreds of) DICOM format images. The DICOM format image may include the metadata such as patient personal information (e.g., patient ID, patient name, patient date of birth (DOB), patient gender) and personal examination information (e.g., a date of examination, accession number of each medical image, and modalities used to perform the examination). Hereinafter, information that includes the medical images, the patient personal information, and the personal examination information is referred to as "patient information."

[System Structure]

FIG. 1 shows a system (1000) in accordance with one or more embodiments. As shown, the system (1000) includes a cloud server (100), a healthcare facility (Facility A, "the healthcare facility") that comprises an imaging device (300), and multiple affiliated facilities (Facility B1-B2), which connects to one another via a network such as Internet. The number of healthcare facilities, affiliated facilities, or users is not limited to this or any other illustrated example. Thus, in the descriptions that follow, specific references made to a "first user," "second user," "Facility B1," "Facility B2," etc. should be understood as mere examples.

[Cloud Server]

The cloud server (100) includes a universal viewer computing device (110) that is installed with the universal viewer application. The universal viewer computing device (110) includes a processor (120), a storage (130) that stores a database to be described later, and a cloud gateway (GW) device (140). The universal viewer computing device (110) may be an industrial-use computer that includes one or more computer processors, associated memory (e.g., random access memory (RAM), cache memory, flash memory, etc.), one or more storage devices (e.g., a hard disk, an optical drive such as a compact disk (CD) drive or digital versatile disk (DVD) drive, a flash memory stick, etc.), and numerous other elements and functionalities. The universal viewer computing device (110) may be managed by the vendor(s) that provide the services of the cloud-based PACS.

In one or more embodiments, the processor (120) receives one or more medical images and examination order information from the healthcare facility (Facility A). The processor (120) correlates the received medical images to the examination order information, and adds the medical images and the examination order information to the patient information stored in the database of the storage (130).

The medical images are created by the imaging device (300) of Facility A in response to the examination order information sent by the first user from one of the affiliated facilities (e.g., Facility B1).

The examination order information is sent from Facility B1 to request Facility A to capture one or more medical image(s) of a patient. The examination order information includes patient-specific information of the patient and first user specific information. The patient-specific information identifies the certain patient whose medical image(s) are requested by the first user, and may include an ID and name of the certain patient. The first user specific information identifies the first user, and may include a unique ID/password of the first user and/or a common ID/password of Facility B1.

The processor (120) also correlates the medical images to disclosure propriety information stored in the database of the storage (130). The disclosure propriety information indicates whether to allow the patient information to be disclosed to another user (second user) who belongs to one of the affiliated facilities (e.g., Facility B2). In one or more embodiments, the disclosure propriety information indicates a status of the patient information. For example, the status may be a first status that prohibits disclosure of the patient information to the second user, a second status that allows disclosure of the patient information to the second user, or a third status allows disclosure of the patient information to the second user only under a predetermined condition. Further, the disclosure propriety information may be set, for example, by the patient or healthcare professionals (e.g., a doctor, nurse, medical staff, medical technician, etc.) at Facility A or by the first user at Facility B1, and sent to the cloud server (100) and stored in the database of the storage (130) in advance.

Furthermore, the processor (120) receives the viewing request sent by the second user from Facility B2. The viewing request is a request for causing the cloud server (100) to allow the second user to view the patient information of a target patient. The viewing request includes patient-specific information of the target patient and viewer specific information. The patient-specific information identifies the target patient whose patient information is requested, and may include an ID and name of the target patient. The viewer specific information identifies a viewer or the second user, and may include a unique ID/password of the second user or a common ID/password of Facility B2.

Further, the processor (120) determines whether to approve the viewing request based on the examination order information or the disclosure propriety information, e.g., by determining whether the viewer specific information coincides with or is correlated to the first user specific information.

The viewer specific information may coincide with the first user specific information when the viewer specific information (e.g., the unique ID of the viewer) is the same as the first user specific information (e.g., the unique ID of the first user), which would indicate that the viewer is the first user. Meanwhile, the viewer specific information may be correlated to the first user specific information when the viewer specific information (e.g., the unique password of the viewer) is not the same as but is linked to the first user specific information (e.g., the unique password of the first user). This may include, for example, a case where the first user is a doctor and the viewer or the second user is a nurse who belongs to the same affiliated facility as the doctor. The correlation of the first user specific information and the viewer specific information (i.e., whether they are correlated to each other) may be set, for example, by the first user at Facility B1, and sent to the cloud server (100) and stored in the database of the storage (130) in advance.

The processor (120) further determines whether to approve the viewing request based on the disclosure propriety information corresponding to the medical image(s) of the target patient, e.g., by determining the statuses the disclosure propriety information and approves or denies the viewing request based on the determination result. In one or more embodiments, the processor (120) may make the determination based on a first status, second status, or third status. For example, the processor (120) may: (i) deny the viewing request upon determining that the disclosure propriety information indicates the first status; (ii) approve the viewing request upon determining that the disclosure propriety information indicates the second status; or (iii) approve the viewing request but only under a predetermined condition (discussed below) upon determining that the disclosure propriety information indicates the third status.

In one or more embodiments, the predetermined condition may be set by and sent to the cloud server by any affiliated facility. Thus, for example, the predetermined condition may be set by the first user at Facility B1, and sent to the cloud server (100) and stored in the database of the storage (130) in advance.

The predetermined condition may also be defined in a variety of ways to suit the needs or preferences of the affiliated facilities and their users. For example, the predetermined condition may be that the target patient has had at least one official appointment (e.g., doctor's appointment) with more than one affiliated facility. Thus, in one or more embodiments, the predetermined condition may be met when the target patient had at least one appointment with not only the first user at Facility B1 but also the second user at Facility B2. As another example, the predetermined condition may be that a user at one affiliated facility has given advance permission to a user at another affiliated facility to view the patient information of the target patient. Thus, in one or more embodiments, the predetermined condition may be met when the first user at Facility B1 gives permission, in advance, to the second user at Facility B2 to view the patient information of the target patient.

When the disclosure propriety information indicates the second status, the processor (120) approves the viewing request for the second user to view the patient information, and transmits the patient information of the target patient to Facility B2 from which the viewing request was sent. The processor (120) would do the same when the disclosure propriety information indicates the third status and the predetermined condition is met.

One or more embodiments may also set a predetermined time limit for users to view the patient information. In one or more embodiments, the processor (120) sets a predetermined time limit during which the second user is allowed to view the patient information. In this case, the processor (120) transmits the setting of the predetermined time limit to Facility B2 to allow the second user to view the patient information within the predetermined time limit After the predetermined time limit has passed, the status of the patient information automatically returns to an original status, namely, a status that prohibits disclosure of the patient information to the second user.

The predetermined time limit may be set to any period suitable for the situation. In one or more embodiments, this may be 30 minutes, one hour, three hours, six hours, one day, etc. Further, in one or more embodiments, the predetermined time limit may be set by the patient or the healthcare professionals at Facility A or by the first user at Facility B1, and sent to the cloud server (100) and stored in the database of the storage (130) in advance.

Still referring to FIG. 1, in one or more embodiments, the processor (120) receives a filtering request sent by the second user from Facility B2 from which the viewing request has been sent. The filtering request is a request for the cloud server (100) to allow the second user to view one or more pieces of the patient information among a plurality of pieces of patient information. The filtering request may include, for example, target item information and the viewer specific information. The target item information specifies the one or more pieces of the patient information among the plurality of pieces of patient information (e.g., patient name, date of birth, date of examination, examined portion, and medical images).

Upon receiving the filtering request, the processor (120) searches a database of the storage (130) for the one or more pieces of the patient information, and transmits the one or more pieces of the patient information to Facility B2 from which the filtering request has been sent.

In one or more embodiments, the processor (120) may correlate disclosure prohibition information to the medical image in the storage (130). The disclosure prohibition information indicates whether to prohibit the patient information from being disclosed. The processor (120) may determine whether to prohibit the patient information from being disclosed based on the disclosure prohibition information. Upon determining to prohibit the patient information from being disclosed, the processor (120) prohibits the patient information from being disclosed regardless of the determination made based on the disclosure propriety information. The disclosure prohibition information may be set, for example, by the patient or the healthcare professionals at Facility A or by the first user at Facility B1, and sent to the cloud server (100) and stored in the database of the storage (130) in advance.

In one or more embodiments, the processor (120) may be configured with a Web-Client (web-CL) application for the universal viewer computing device (110) that allows each of the facilities (Facility A-C) to access the universal viewer application via a web-browser. For example, the universal viewer application may be accessed as a web page by inputting a uniform resource locator (URL) (e.g., a web address) associated with the web-CL into the search bar of the web-browser.

In one or more embodiments, the storage (130) is configured as a remote medical repository that stores the database remotely on the cloud server (100). For example, the remote medical repository may be a virtual data room (VDR) or a database (or group of databases) accessed remotely via the Internet.

The database of the storage (130) stores (i) the patient information including the medical images, the patient personal information, and the personal examination information, (ii) the examination order information, (iii) the disclosure propriety information, and (iv) the disclosure prohibition information. The database may also store the correlation of the first user specific information and the viewer specific information, the predetermined condition for approving the viewing request, and the predetermined time limit during which the second user is allowed to view the patient information, as described above.

FIGS. 2-5 show example tables of the database stored in the storage (130) according to one or more embodiments.

FIG. 2 shows a table of the patient information according to one or more embodiments. The patient information includes the personal examination information (Examination ID), the patient personal information (Patient ID), and the medical images (Image Data).

FIG. 3 shows a table of the personal examination information according to one or more embodiments. The personal examination information includes Examination ID ("111," "222," "333," etc.), Order ID ("Order 1," "Order 2," "Order 3," etc.), Examined portion ("Leg Part," "Head," "Chest," etc.), and Doctor/Radiologist ("Doctor X," "Radiologist Y," "Doctor Z," etc.). The personal examination information may further include medical records including examination results, report of examination, etc., though not illustrated.

FIG. 4 shows a table of the patient personal information according to one or more embodiments. The patient personal information includes Patient ID ("Patient 1," "Patient 2," "Patient 3," etc.), Flag ("1," "2," "3," etc.), Patient Name ("Bob," "Mary," "John," etc.), Gender ("Male," "Female," "Male," etc.), and Date of Birth ("1980/1/1," "2010/4/1," "1995/6/30" etc.). In one or more embodiments, the disclosure propriety information is a flag indicating a status of: "1" that prohibits disclosure of the patient information to the second user; "2" that allows disclosure of the patient information to the second user; or "3" that allows disclosure of the patient information to the second user only under the predetermined condition.

FIG. 5 shows a table of the flag as the disclosure propriety information according to one or more embodiments. The table shows the status of "1: Deny," "2: Approve," and "3: Conditionally Approve."

In one or more embodiments, a cloud gateway (GW) device (140) may be a hub or a local area network (LAN) at the facility where the cloud server (100) is physically disposed. The cloud GW device (140) may be configured as a relay point between the cloud server (100) and the healthcare facilities (Facility A-C) that enables each of the healthcare facilities (Facility A-C) to communicate and share (i.e., retrieve and transmit) medical images with the cloud server (100).

[Facilities]

(Healthcare Facility with Imaging Device)

Returning to FIG. 1, the system (1000) further includes, at Facility A, a local computing device (200) (i.e., local computer) and an imaging device (300) connected or detachably attached to the local computing device (200). Facility A may be any type of facility that captures medical images of patients and provides medical care, such as a public hospital, a university hospital, a national hospital, etc.

The local computing device (200) may correspond to a personal computer (PC), a laptop, a server, etc. In one or more embodiments, the local computing device (200) may include a processor (210), a storage (220), a universal viewer client application (230), an I/O interface (240), and a local gateway (GW) device (250).

The processor (210) manages the medical images captured by the imaging device (300) and stored in the storage (220). The universal viewer client application (230) causes the I/O interface (240) to display the contents associated with the universal viewer client application (230) (e.g., the GUI, the medical images, etc.) and receives input commands via the I/O interface (240). The I/O interface (240) may include an input device such as a touchscreen, keyboard, mouse, microphone, touchpad, electronic pen, or any other type of input device. The I/O interface (240) may also include an output device such as a screen (e.g. a liquid crystal display (LCD), a plasma display, touchscreen, cathode ray tube (CRT) monitor, projector, or any other display device), a printer, external storage, or any other output devices. The local GW device (250) synchronizes the locally-managed and stored data with the cloud server (100).

The imaging device (300) may correspond to any type of image capturing device, such as a portable radiographic image capturing device, a cassette-type digital X-ray imaging device, etc. The number of imaging devices is not limited to the illustrated example.

Upon receiving the examination order information from Facility B1, the processor (210) returns the medical image(s) captured by the image device (300) to Facility B1. Furthermore, the processor (210) transmits the medical image(s), together with the patient personal information and the personal examination information, to the cloud server (100).

The storage (220) may store the examination order information, and the patient information that includes the medical images, the patient personal information, and the personal examination information.

(Affiliated Facilities)

Still referring to FIG. 1, in one or more embodiments, the system (1000) further includes local computing devices (400B1-B2) (i.e., local computers) in Facilities B1-B2. Facilities B1-B2 may be any type of facility that provides medical care such as a public hospital, a private hospital, a medical clinic, a dental clinic, an emergency vehicle (e.g., ambulance), a mobile clinic vehicle, etc. Each of the local computing devices (400B1-B2) may correspond to a personal computer (PC), a laptop, a mobile computing device (e.g., tablet PC, smartphone, etc.), a server, a mainframe, a kiosk, etc.

In one or more embodiments, the local computing devices (400B1-B2) may include processors (410B1-B2), storages (420B1-B2), universal viewer client applications (430B1-B2), and I/O interfaces (440B1-B2), which have substantially similar functions to those of the local computing device (200). The local computing devices (400B1-B2) of Facilities B1-B2 may only include the minimum required systems such as the universal viewer client applications (430B1-B2) to be able to share (i.e., retrieve and transmit) data with the universal viewer computing device (110).

In one or more embodiments, the processor (410B1) may transmit, to Facility A, the examination order information based on inputs by the first user via the I/O interface (440B1). Upon receiving the medical images from Facility A, the processor (410B1) may store the medical images in the storage (420B1).

Furthermore, the processor (410B2) may transmit, to the cloud server (100), the viewing request based on inputs by the second user via the I/O interface (440B2). The processor (410B2) may also transmit, to the cloud server (100), the filtering request based on inputs by the second user via the I/O interface (440B2).

Once the cloud server (100) allows the second user to view the patient information, the processors (410B2) receives the patient information from the cloud server (100), and the I/O interface (440B2) display the patient information on the screens.

In one or more embodiments, the local computing devices (400B1-B2) may be zero-footprint client terminals. The zero-footprint client terminals are independent from a specific operating system (OS), and applications delivered from the cloud server (100) leave no footprint (i.e., data) in the zero-footprint client terminals. Some of the zero-footprint client terminals store application data as cache. For example, the zero-footprint client terminals used in the affiliated facilities store no patient data therein, but store the data as cache on a browser. Such browser applications include HTML5 and JavaScript®. The zero-footprint client terminals are suitable for Facilities B1-B2, because a large data capacity for storing the patient information is not required. This also eliminates risk of information leakage, and protects the security of the patient information appropriately.

[Process for Approving Viewing Request Based on Disclosure Propriety Information]

Figure 6:
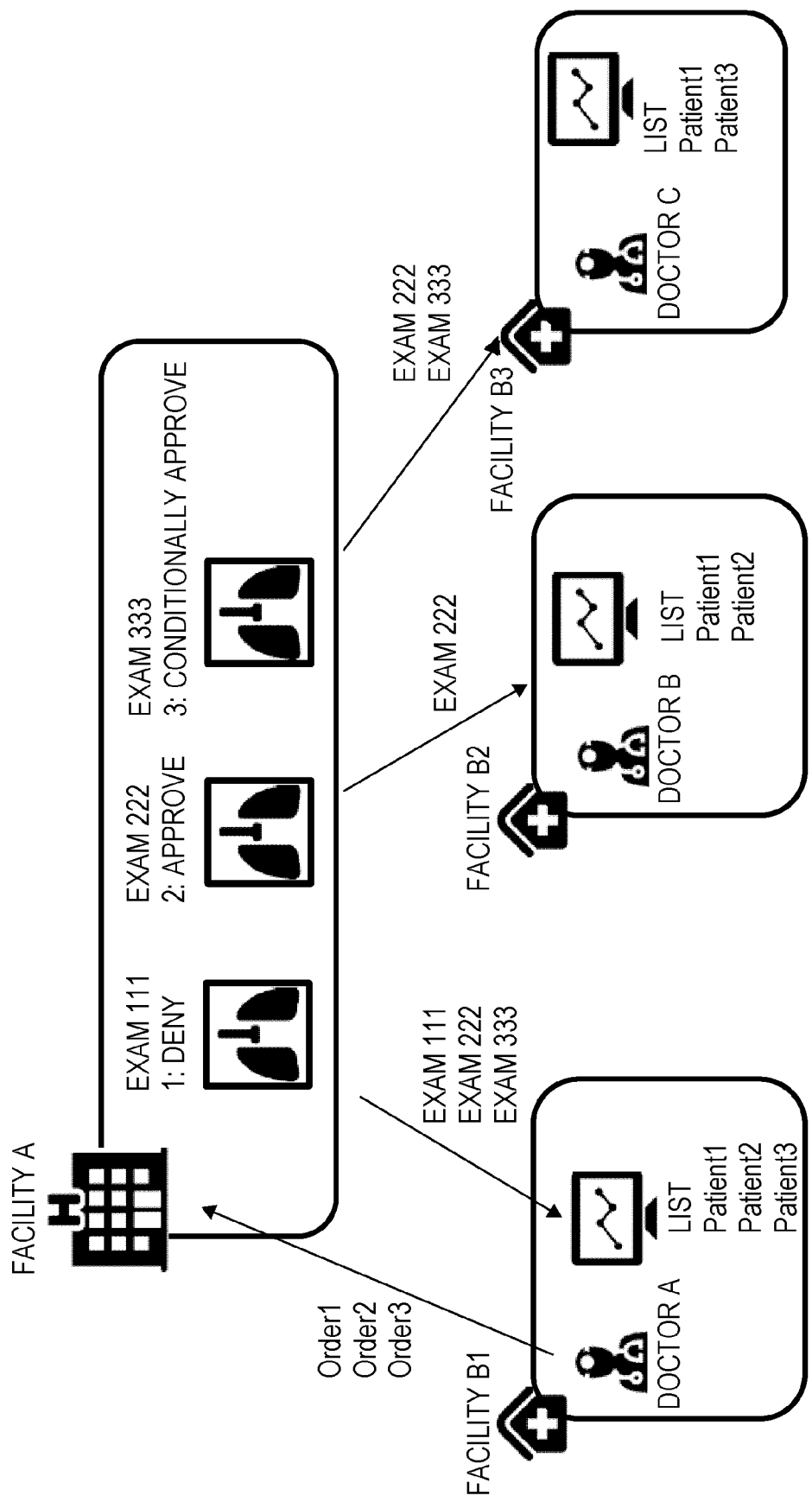
FIG. 6 shows a schematic diagram illustrating how to approve a viewing request based on disclosure propriety information according to one or more embodiments.

Next, approve a viewing request based on the disclosure propriety information, i.e., flags, according to one or more embodiments will be described with reference to FIG. 6. In the example of FIG. 6, the second user may belong to not only Facility B2 but also Facility B3. For simplicity's sake, the cloud server (100) is not shown in this figure.

In FIG. 6, in response to the examination order information (Order 1-3) from Facility B1, the cloud server (100) obtains from Facility A the medical images of three patients (Patient 1-3) acquired by three examinations (Exam 111-333).

In the storage (130) of the cloud server (100), a flag corresponding to a first medical image of Exam 111 is set to "1: Deny." A flag corresponding to a second medical image of Exam 222 is set to "2: Approve." A flag corresponding to a third medical image of Exam 333 is set to "3: Conditionally Approve." The predetermined condition is met when the target patient had at least one appointment not only at Facility B1 but also at Facility B2 or B3.

In this case, the first user can view all the medical images of Exam 111-333 because the first user requested the medical images from Facility B1. The second user at Facility B2 can view only the second medical image of Exam 222 because the flag of the first medical image indicates "1: Deny," and the flag of the third medical image indicates "3: Conditionally Approve" but Patient 3 did not have any appointment at Facility B2. Meanwhile, the second user at Facility B3 can view the second and third medical images of Exam 222-333, because Patent 3 had at least one appointment at Facility B3.

[Operations in Affiliated Facility]

Next, operations for sending the viewing request and the filtering request will be described with reference to FIG. 7, which shows example screenshots of the screens displayed on the I/O interface (440B2) at Facility B2.

To send the viewing request to the cloud server (100), the second user inputs a common ID and/or password of Facility B2 on a first login screen. Once the common ID/password are input, a first patient list screen displays a first patient list of Patient A and Patient B for viewing the patient information. The first patient list screen also displays a viewing request button for patient information of Patient C. The second user at Facility B2 has requested the medical images of Patient A, B in the past, but not Patient C.

Once the second user pushes the viewing request button, a security alert screen is displayed with a disclaimer that the user will bear responsibility for preventing the leak of the patient information of Patient C. The second user may agree to the disclaimer by pressing an OK button on the security alert screen.

Once the OK button is pressed, a second login screen is displayed to prompt the second user to input a unique ID and/or password of the second user.

The second login screen may also prompt the second user to input one or more reasons for viewing the medical image(s). The reason for viewing may arise due to any urgent situations or needs for Facility B2. For example, the reason may arise because the medical images urgently need to be viewed in an ambulance. As another example, the reason may arise because the second user needs to view the medical images instead of the first user who is taking a vacation or has retired.

One or more embodiments stores an access history in the database of the storage (420B2), and sends the access history to the cloud server (100). The access history may include the reason for viewing, ID/password of the second user, medical image(s) viewed the second user, time of access, access period, and success/failure of access.

Figure 7:
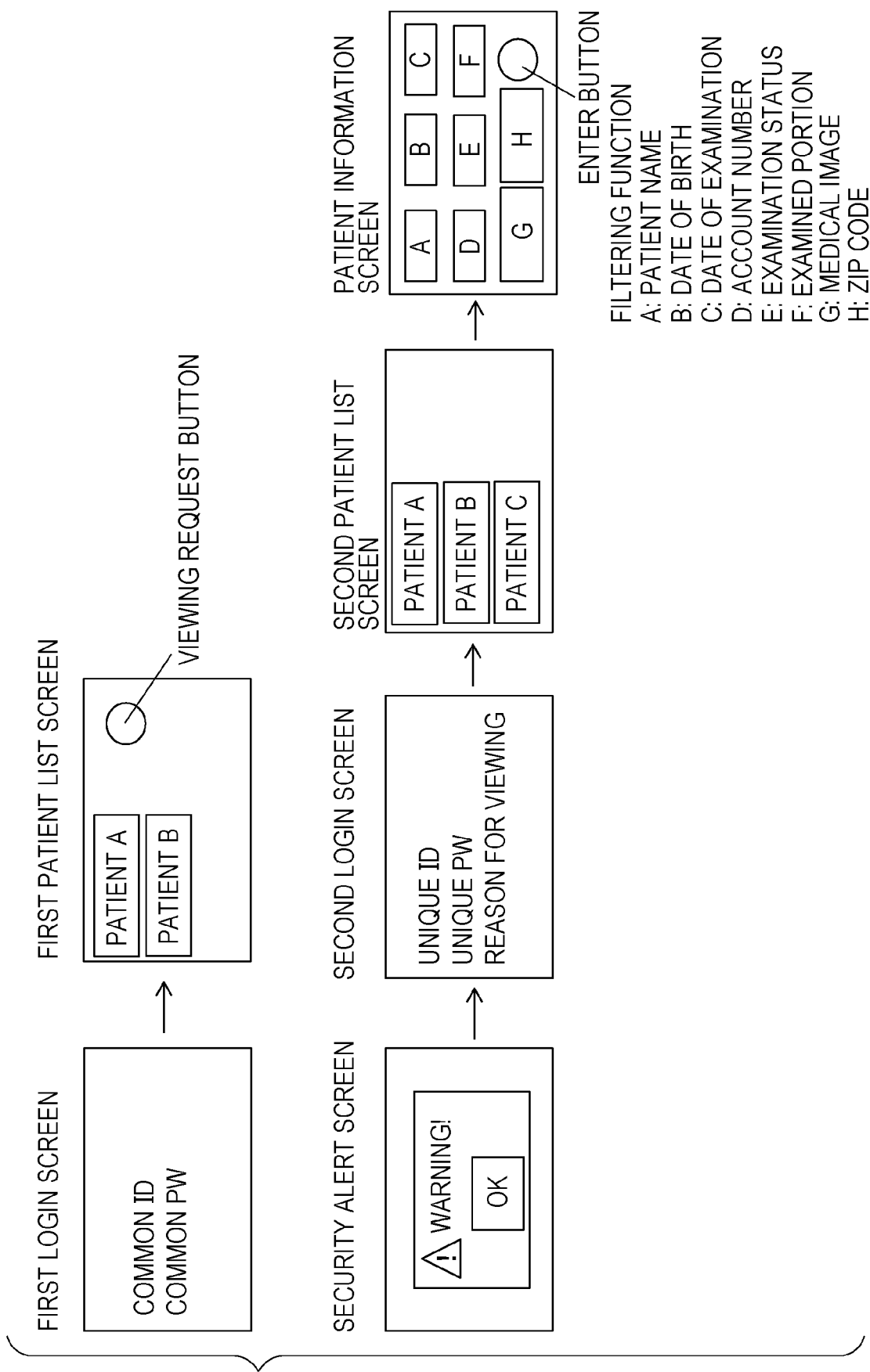
FIG. 7 shows a flow diagram illustrating operations for sending the viewing request and a filtering request from an affiliated facility according to one or more embodiments.

Still referring to FIG. 7, once the second user inputs the unique ID/password and the reason for viewing on the second login screen, a second patient list screen displays a second patient list of Patient A-C for viewing the patient information. To the medical image of Patient C, the flag indicates "2: Approve" in the storage (130) of the cloud server (100).

Once Patient C is selected on the second patient list screen, a patient information screen for Patient C is displayed. The patient information screen may include a plurality of input boxes corresponding to the plurality of pieces of the patient information. In one or more embodiments, the input boxes include "A: Patient Name," "B; Date of Birth," "C: Date of Examination," "D: Account Number," "E: Examination Status," "F: Examined Portion," "G: Medical Image," and "H: Zip code."

In one or more embodiments, the patient information screen may have a filtering function. Once the second user checks one or more input boxes (e.g., "F: Examined Portion" and "G: Medical Image") and pushes an enter button, the patient information screen displays only the patient information (e.g., "Examined Portion: Chest" and the medical image of the chest) corresponding to the selected input boxes. In one or more embodiments, once the second user inputs known information (e.g., a Zip code) in at least one of the boxes (e.g., "H: Zip code") and pushes the enter button, the patient information screen also displays other information in the remaining boxes. By this, the second user can obtain the necessary patient information more effectively while protecting the security of the patient information.

[Viewing Control Method]

Figure 8:
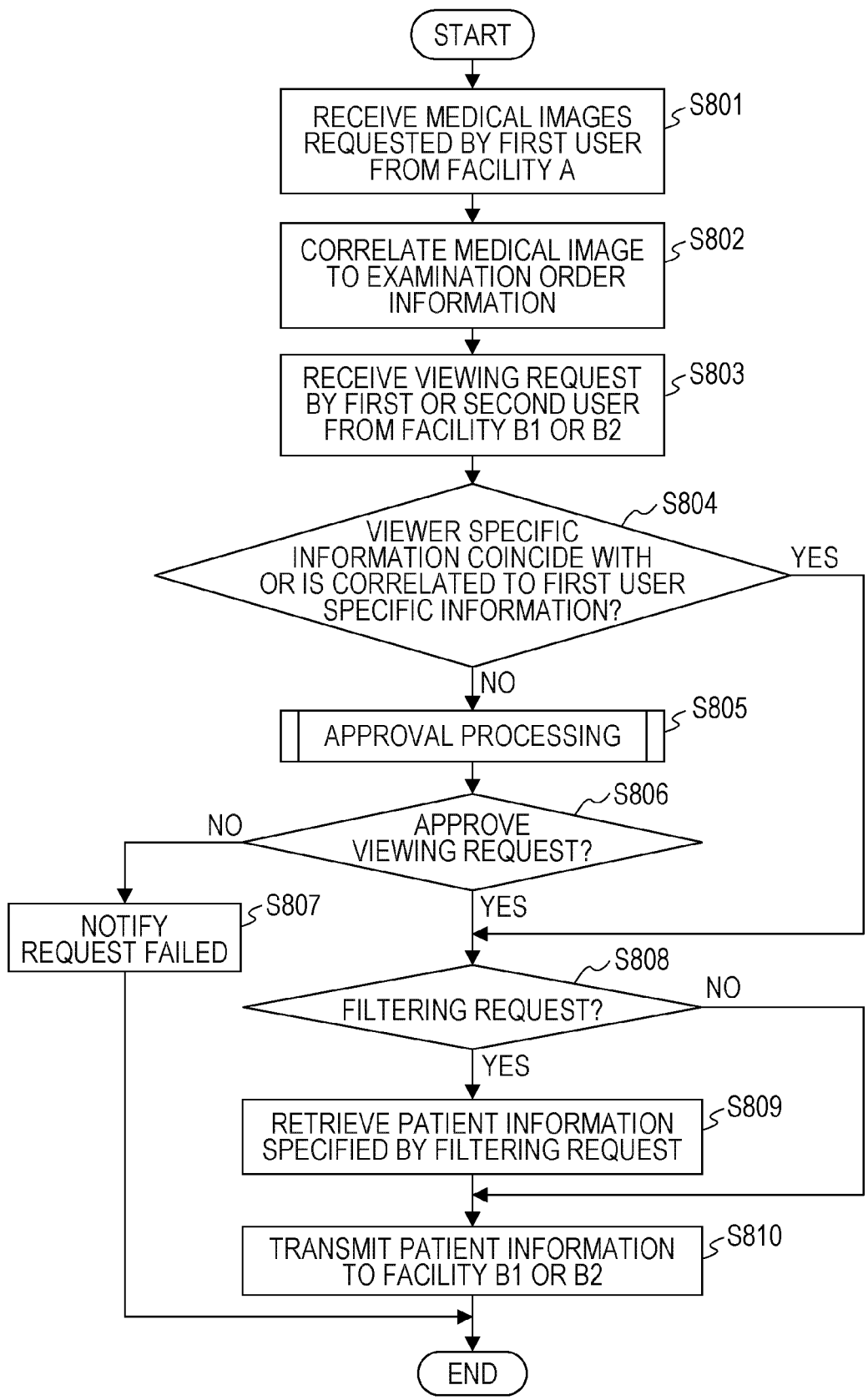
FIG. 8 shows a main flowchart according to one or more embodiments.

Now a viewing control method according to one or more embodiments will be described with reference to FIG. 8. One or more of the steps in FIG. 8 may be performed by the components of the system 1000, discussed above in reference to FIG. 1. In one or more embodiments, one or more of the steps shown in FIG. 8 may be omitted, repeated, and/or performed in a different order than the order shown in FIG. 8. Accordingly, the scope of the invention should not be considered limited to the specific arrangement of steps shown in FIG. 8.

First, upon receiving the medical images from Facility A (Step S801), the cloud server (100) correlates the medical images to the examination order information, and adds the medical images and the examination order information to the patient information stored in the database of the storage (130) (Step S802).

Upon receiving the viewing request from Facility B1 or B2, the cloud server (100) determines whether the viewer specific information coincides with or is correlated to the first user specific information (S804).

Upon determining that the viewer specific information coincides with or is correlated to the first user specific information (S804: YES), the cloud server (100) approves the viewing request, and the processing proceeds to Step S808.

Upon determining that the viewer specific information does not coincide with and is not correlated to the first user specific information (S804: NO), an approval processing is performed (Step S805).

Upon determining to deny the viewing request as a result of the approval processing (Step S806: NO), the cloud server (100) informs Facility B2 of the result and the processing is terminated.

Meanwhile, upon determining to approve the viewing request (Step S806: YES), the processing proceeds to the next step, and the cloud server (100) determines whether the filtering request has been received (Step S808).

Upon receiving the filtering request (Step S808: YES), the cloud server (100) searches the database of the storage (130) for the selected patient information by the filtering request (Step S809). The cloud server (100) then transmits the selected patient information to Facility B2 (Step S810) and the processing is terminated.

In the case that the filtering request has not been received (Step S808: NO), the cloud server (100) transmits the patient information without searching specific pieces of the patient information (Step S810) and the processing is terminated.

Figure 9:
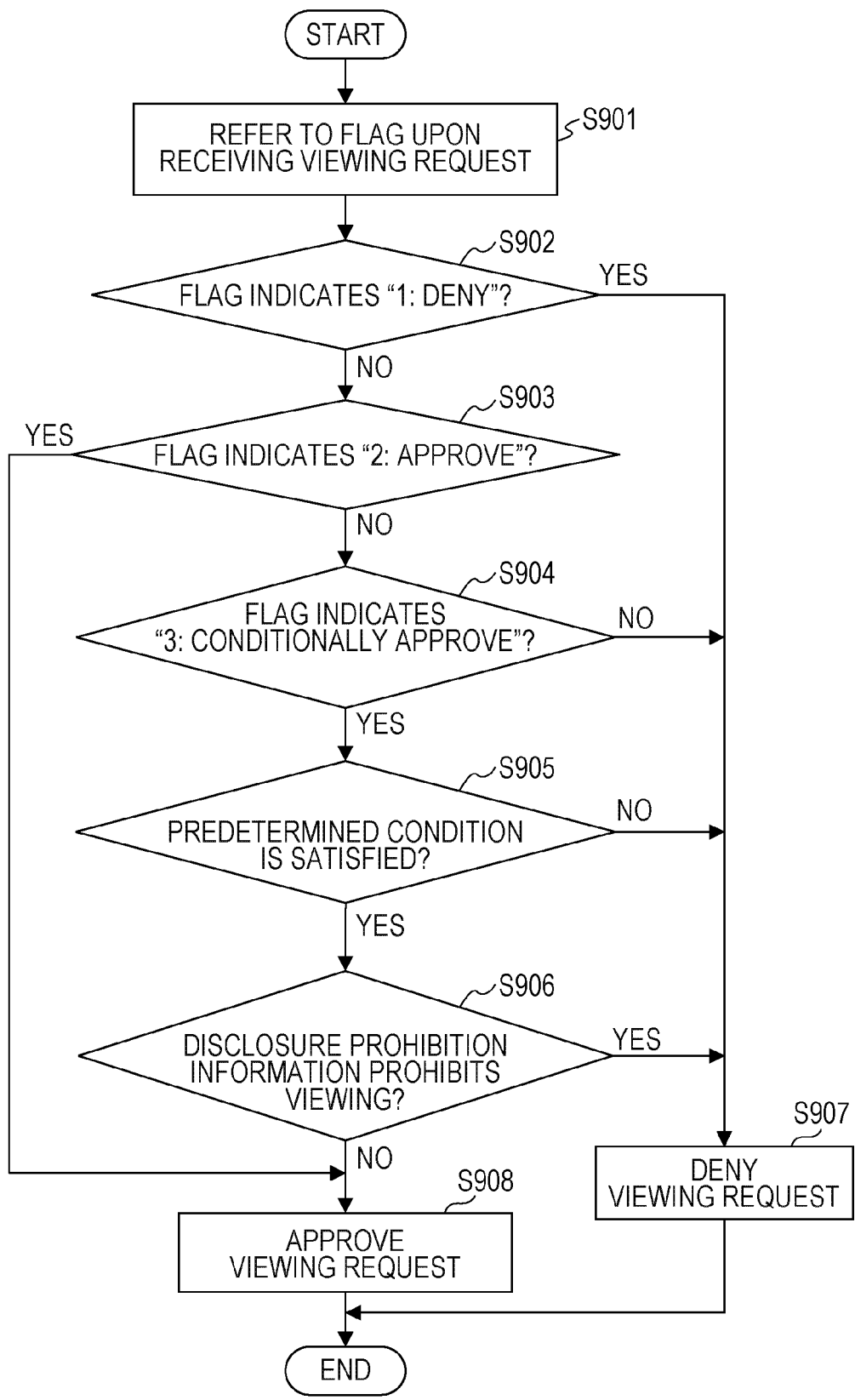
FIG. 9 shows a flowchart of approval processing according to one or more embodiments.

Next, the approval processing will be described with reference to FIG. 9. One or more of the steps in FIG. 9 may be performed by the components of the system 1000, discussed above in reference to FIG. 1. In one or more embodiments, one or more of the steps shown in FIG. 9 may be omitted, repeated, and/or performed in a different order than the order shown in FIG. 9. Accordingly, the scope of the invention should not be considered limited to the specific arrangement of steps shown in FIG. 9.

Upon receiving the viewing request, the cloud server (100) refers to the flag to confirm the status of the patient information (Step S901).

Firstly, the cloud server (100) determines whether the flag indicates the first status (Step S902).

Upon determining that the flag indicates the first status (Step S902: YES), the cloud server (100) determines to deny the viewing request (Step S907), and the processing is terminated. Upon determining that the flag does not indicate the first status (Step S902: NO), the processing proceeds to the next step.

Secondly, the cloud server (100) determines whether the flag indicates the second status (Step S903). Upon determining that the flag indicates the second status (Step S903: YES), the cloud server (100) determines to approve the viewing request (Step S908), and the processing is terminated. Upon determining that the flag does not indicate the second status (Step S903: NO), the processing proceeds to the next step.

Thirdly, the cloud server (100) determines whether the flag indicates the third status (Step S904). Upon determining that the flag does not indicate the third status (Step S904: NO), the cloud server (100) determines to deny the viewing request (Step S907), and the processing is terminated. Upon determining that the flag indicates the third status (Step S904: YES), the processing proceeds to the next step.

Next, the cloud server (100) determines whether the predetermined condition is satisfied (Step S905). Upon determining that the predetermined condition is not satisfied (Step S905: NO), the cloud server (100) determines to deny the viewing request (Step S907), and the processing is terminated. Upon determining that the predetermined condition is satisfied (Step S905: YES), the processing proceeds to the next step.

Then, the cloud server (100) refers to the disclosure prohibition information to confirm whether viewing of the patient information is prohibited (Step S906). Upon determining that the disclosure prohibition information prohibits the viewing (Step S906: YES), the cloud server (100) determines to deny the viewing request (Step S907), and the processing is terminated. Upon determining that the disclosure prohibition information does not prohibit the viewing (Step S906: NO), the cloud server (100) determines to approve the viewing request (Step S908), and the processing is terminated.

Figure 10:
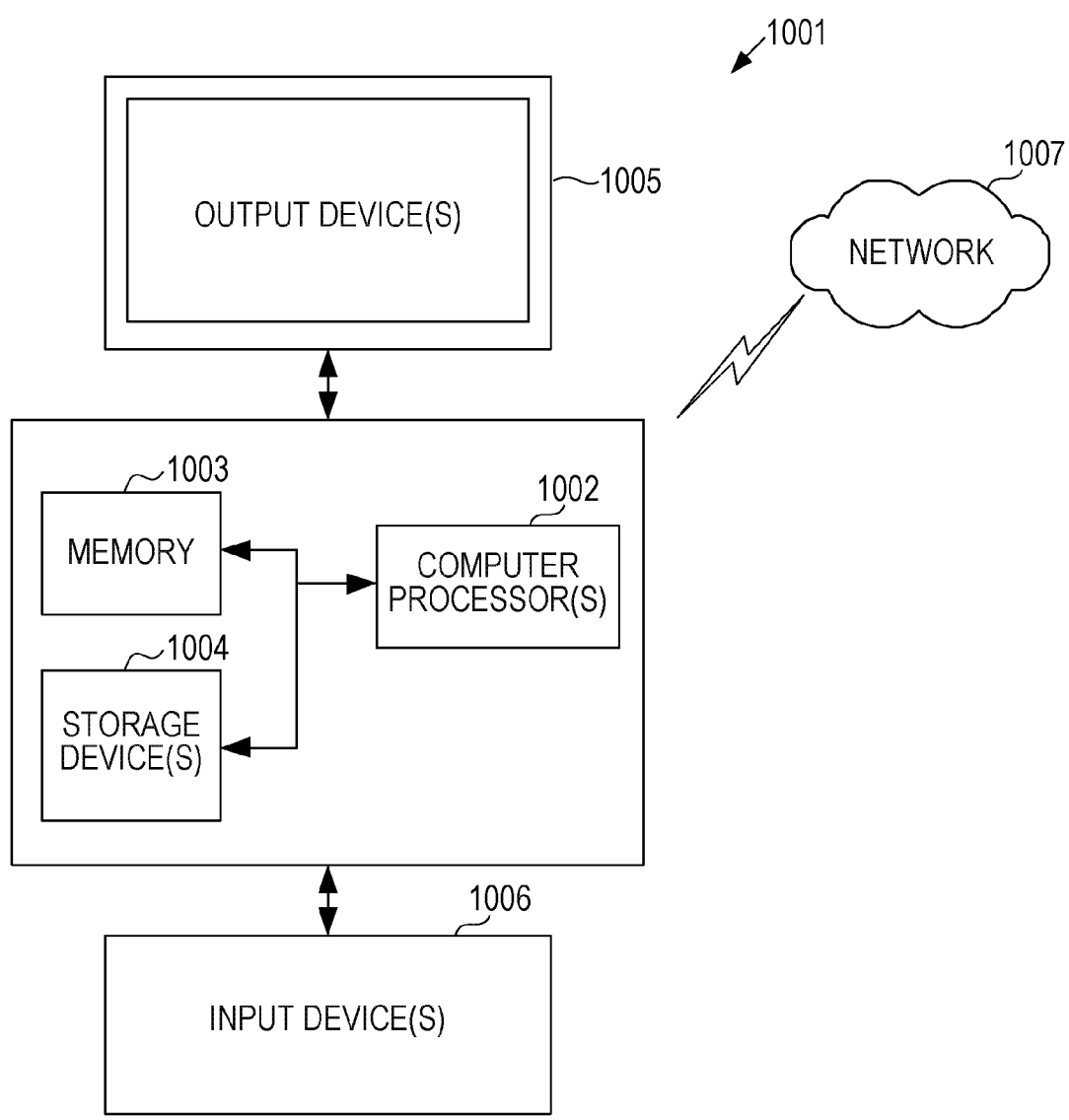
FIG. 10 shows a computing system in accordance with one or more embodiments.

Embodiments of the invention may be implemented on virtually any type of computing system, regardless of the platform being used. For example, the computing system may be one or more mobile devices (e.g., laptop computer, smart phone, personal digital assistant, tablet computer, or other mobile device), desktop computers, servers, blades in a server chassis, or any other type of computing device or devices that includes at least the minimum processing power, memory, and input and output device(s) to perform one or more embodiments. For example, as shown in FIG. 10, the computing system (1001) may include one or more computer processor(s) (1002), associated memory (1003) (e.g., random access memory (RAM), cache memory, flash memory, etc.), one or more storage device(s) (1004) (e.g., a hard disk, an optical drive such as a compact disk (CD) drive or digital versatile disk (DVD) drive, a flash memory stick, etc.), and numerous other elements and functionalities. The computer processor(s) (1002) may be an integrated circuit for processing instructions. For example, the computer processor(s) may be one or more cores, or micro-cores of a processor. The computing system (1001) may also include one or more input device(s) (1006), such as a touchscreen, keyboard, mouse, microphone, touchpad, electronic pen, or any other type of input device. Further, the computing system (1001) may include one or more output device(s) (1005), such as a screen (e.g., a liquid crystal display (LCD), a plasma display, touchscreen, cathode ray tube (CRT) monitor, projector, or other display device), a printer, external storage, or any other output device. One or more of the output device(s) may be the same or different from the input device(s). The computing system (1001) may be connected to a network (1007) (e.g., a local area network (LAN), a wide area network (WAN) such as the Internet, mobile network, or any other type of network) via a network interface connection (not shown). The input and output device(s) may be locally or remotely (e.g., via the network (1007)) connected to the computer processor(s) (1002), memory (1003), and storage device(s) (1004). Many different types of computing systems exist, and the aforementioned input and output device(s) may take other forms.

Software instructions in the form of computer readable program code to perform embodiments of the invention may be stored, in whole or in part, temporarily or permanently, on a non-transitory computer readable medium such as a CD, DVD, storage device, a diskette, a tape, flash memory, physical memory, or any other computer readable storage medium. Specifically, the software instructions may correspond to computer readable program code that when executed by a processor(s), is configured to perform embodiments of the invention.

Further, one or more elements of the aforementioned computing system (1001) may be located at a remote location and connected to the other elements over a network (1007). Further, one or more embodiments of the invention may be implemented on a distributed system having a plurality of nodes, where each portion of the invention may be located on a different node within the distributed system. In one embodiment of the invention, the node corresponds to a distinct computing device. Alternatively, the node may correspond to a computer processor with associated physical memory. The node may alternatively correspond to a computer processor or micro-core of a computer processor with shared memory and/or resources.

The method, non-transitory computer readable medium, and system of one or more embodiments provide various improvements to viewing technologies in the medical field. For example, the cloud server determines whether to approve the viewing request to view the patient information from the first user or the second user based on the examination order information or the disclosure propriety information. According to this feature, the viewing request from the first user can be approved based on the examination order information, and the viewing request from the second user can be conditionally approved based on the disclosure propriety information. As a result, also the second user who has not requested the examination can view the patient information under the predetermined condition. Thus, the second user can view the patient information, for example, as required in medical care and/or in case of emergency, and thereby convenience of the system is improved while protecting the security of the patient information.

According to one or more embodiments, the cloud server approves the viewing request not only in the case that the viewer specific information coincides with the first user specific information, but also the viewer specific information is correlated to the first user specific information. According to this feature, accessibility to the patient information is improved while protecting the security of the patient information.

According to one or more embodiments, in the case that the predetermined time limit is set, the second user can view the patient information only during the predetermined time limit According to this feature, the second user who has not requested the examination can view the patient information only under exceptional circumstances (e.g., medical emergencies), and security of the patient information is protected appropriately. After the predetermined time limit has passed, the status of the patient information automatically returns to the status that prohibits disclosure of the patient information to the second user. According to this feature, convenience of the system is further improved.

According to one or more embodiments, by sending the filtering request, the first user or the second user can view only certain pieces of patient information. According to this feature, the first user or the second user can view only necessary patient information, and the system can provide the information more efficiency.

According to one or more embodiments, the cloud server determines whether to approve the viewing request based on the disclosure prohibition information regardless of the determination made based on the disclosure propriety information. According to this feature, the security of the patient information is protected more appropriately.

While the invention has been described with respect to a limited number of embodiments, those skilled in the art, having benefit of this disclosure, will appreciate that other embodiments can be devised which do not depart from the scope of the invention as disclosed herein. Accordingly, the scope of the invention should be limited only by the attached claims.

What is claimed is:

1. A method for managing a plurality of pieces of patient information in a system that shares the patient information among a cloud server comprising a processor and a storage configured as a remote medical repository, a healthcare facility comprising a radiographic image capturing device and an I/O interface, and affiliated facilities comprising an I/O interface, wherein the cloud server, the healthcare facility, the affiliated facilities are connected to one another via a network, the method comprising:

receiving, by the processor from the healthcare facility, a medical image created by the radiographic image capturing device in response to examination order information sent by a first user from one of the affiliated facilities;

correlating, by the processor, the received medical image to the examination order information and adding the medical image and the examination order information to the patient information stored in the storage;

receiving, by the processor from the healthcare facility or the one of the affiliated facilities, disclosure propriety information that is set based on an input to the I/O interface of the healthcare facility or the one of the affiliated facilities;

correlating, by the processor, the medical image to the disclosure propriety information in the storage;

receiving, by the processor, a viewing request sent by the first user from the one of the affiliated facilities that sent the examination order information or a viewing request sent by a second user from another of the affiliated facilities to view the patient information;

determining, by the processor, whether to approve the viewing request based on the examination order information or the disclosure propriety information;

approving, by the processor, the viewing request by the first user from the one of the affiliated facilities or the viewing request by the second user from the other of the affiliated facilities to view the patient information; and transmitting the patient information to the one of the affiliated facilities or the other of the affiliated facilities such that the one of the affiliated facilities or the other of the affiliated facilities can display the patient information on a screen of the I/O interface, wherein the disclosure propriety information is a flag set in a correspondence table of the patient information in the storage and indicating whether the patient information is allowed to be disclosed to the second user at the other of the affiliated facilities that has not sent the examination order information, the flag indicates a status of the patient information that is a first status, a second status, or third status,
      the first status prohibits disclosure of the patient information to the second user at the other of the affiliated facilities;
      the second status allows disclosure of the patient information to the second user at the other of the affiliated facilities; and
      the third status allows disclosure of the patient information to the second user at the other of the affiliated facilities only under a predetermined condition, and
   the method further comprises:
      automatically approving the viewing request for the second user at the other of the affiliated facilities, under the condition that the flag indicates the second status or under the condition that the flag indicates the third status and the predetermined condition is met, wherein
      the predetermined condition includes at least one of:
         a fact that a target patient had at least one appointment to see a doctor with the other of the affiliated facilities in past, and
         a fact that the one of the affiliated facilities permitted the second user at the other of the affiliated facilities to view the patient information.

2. The method according to claim 1, wherein
the examination order information includes first user specific information,
the viewing request includes viewer specific information, and
the determining of whether to approve the viewing request comprises:
   determining whether the viewer specific information coincides with or is correlated to the first user specific information.

3. The method according to claim 1, further comprising:
setting, by the processor, a predetermined time limit during which the second user is allowed to view the patient information; and
transmitting, by the processor, the setting of the predetermined time limit to the one of the affiliated facilities to allow the second user to view the patient information within the predetermined time limit.

4. The method according to claim 1, further comprising:
receiving, by the processor, a filtering request from the one of the affiliated facilities to view one or more pieces of the patient information among the plurality of pieces of the patient information;
searching, by the processor, database in the storage for the one or more pieces of the patient information; and
transmitting, by the processor, the one or more pieces of the patient information to the one of the affiliated facilities.

5. The method according to claim 1, further comprising:
correlating, by the processor, disclosure prohibition information to the medical image in the storage, wherein the disclosure prohibition information indicates whether to prohibit the patient information from being disclosed;
determining, by the processor, whether to prohibit the patient information from being disclosed based on the disclosure prohibition information, and
prohibiting, by the processor, the patient information from being disclosed regardless of the determination made based on the flag.

6. A non-transitory computer-readable medium (CRM) storing an instruction that causes a cloud server to perform an operation for managing a plurality of pieces of patient information in a system that shares the patient information among a cloud server comprising a processor and a storage configured as a remote medical repository, a healthcare facility comprising a radiographic image capturing device and an I/O interface, and affiliated facilities comprising an I/O interface, wherein the cloud server, the healthcare facility, and the affiliated facilities are connected to one another via a network, the operation comprising causing the processor of the cloud server to:

receive, from the healthcare facility, a medical image created by the radiographic image capturing device in response to examination order information sent by a first user from one of the affiliated facilities;

correlate the received medical image to the examination order information and add the medical image and the examination order information to the patient information stored in the storage;

receive, from the healthcare facility or the one of the affiliated facilities, disclosure propriety information that is set based on an input to the I/O interface of the healthcare facility or the one of the affiliated facilities;

correlate the medical image to the disclosure propriety information in the storage;

receive a viewing request sent by the first user from the one of the affiliated facilities that sent the examination order information or a viewing request sent by a second user from another of the affiliated facilities to view the patient information;

determine whether to approve the viewing request based on the examination order information or the disclosure propriety information;

approve the viewing request by the first user from the one of the affiliated facilities or the viewing request by the second user from the other of the affiliated facilities to view the patient information; and transmit the patient information to the one of the affiliated facilities or the other of the affiliated facilities such that the one of the affiliated facilities or the other of the affiliated facilities can display the patient information on a screen of the I/O interface, wherein the disclosure propriety information is a flag set in a correspondence table of the patient information in the storage and indicating whether the patient information is allowed to be disclosed to the second user at the other of the affiliated facilities that has not sent the examination order information, the flag indicates a status of the patient information that is a first status, a second status, or third status,
  the first status prohibits disclosure of the patient information to the second user at the other of the affiliated facilities;
  the second status allows disclosure of the patient information to the second user at the other of the affiliated facilities; and
  the third status allows disclosure of the patient information to the second user at the other of the affiliated facilities only under a predetermined condition, and the processor of the cloud server automatically approves the viewing request for the second user at the other of the affiliated facilities, under the condition that the flag indicates the second status or under the condition that the flag indicates the third status and the predetermined condition is met, wherein the predetermined condition includes at least one of:
  a fact that a target patient had at least one appointment to see a doctor with the other of the affiliated facilities in past, and
  a fact that the one of the affiliated facilities permitted the second user at the other of the affiliated facilities to view the patient information.

7. The non-transitory CRM according to claim 6, wherein the examination order information includes first user specific information,
the viewing request includes viewer specific information, and
when determining whether to approve the viewing request, the cloud server determines whether the viewer specific information coincides with or is correlated to the first user specific information.

8. The non-transitory CRM according to claim 6, wherein the operation further comprises causing the processor of the cloud server to:
set a predetermined time limit during which the second user is allowed to view the patient information; and
transmit the setting of the predetermined time limit to the one of the affiliated facilities to allow the second user to view the patient information within the predetermined time limit.

9. The non-transitory CRM according to claim 6, wherein the operation further comprises causing the processor of the cloud server to:
receive a filtering request from the one of the affiliated facilities to view one or more pieces of the patient information among the plurality of pieces of the patient information;
search database in the storage for the one or more pieces of the patient information; and
transmit the one or more pieces of the patient information to the one of the affiliated facilities.

10. The non-transitory CRM according to claim 6, wherein the operation further comprises causing the processor of the cloud server to:
correlate disclosure prohibition information to the medical image in the storage, wherein the disclosure prohibition information indicates whether to prohibit the patient information from being disclosed;
determine whether to prohibit the patient information from being disclosed based on the disclosure prohibition information, and
prohibit the patient information from being disclosed regardless of the determination made based on the flag.

11. A system that manages a plurality of pieces of patient information, comprising:
a cloud server that comprises a processor and a storage configured as a remote medical repository;
a healthcare facility that comprises a radiographic image capturing device and an I/O interface; and
affiliated facilities comprising an I/O interface, wherein
the system shares the patient information among the cloud server, the healthcare facility, and the affiliated facilities via a network, and
the processor of the cloud server:
  receives, from the healthcare facility, a medical image created by the radiographic image capturing device in response to examination order information sent by a first user from one of the affiliated facilities;
  correlates the received medical image to the examination order information and adds the medical image and the examination order information to the patient information stored in the storage;

receives, from the healthcare facility or the one of the affiliated facilities, disclosure propriety information that is set based on an input to the I/O interface of the healthcare facility or the one of the affiliated facilities;

correlates the medical image to the disclosure propriety information in the storage;

receives a viewing request sent by the first user from the one of the affiliated facilities that sent the examination order information or a viewing request sent by a second user from another of the affiliated facilities to view the patient information;

determines whether to approve the viewing request based on the examination order information or the disclosure propriety information;

approves the viewing request by the first user from the one of the affiliated facilities or the viewing request by the second user from the other of the affiliated facilities to view the patient information; and transmits the patient information to the one of the affiliated facilities or the other of the affiliated facilities sent such that the one of the affiliated facilities or the other of the affiliated facilities can display the patient information on a screen of the I/O interface, wherein the disclosure propriety information is a flag set in a correspondence table of the patient information in the storage and indicating whether the patient information is allowed to be disclosed to the second user at the other of the affiliated facilities that has not sent the examination order information, the flag indicates a status of the patient information that is a first status, a second status, or third status, the first status prohibits disclosure of the patient information to the second user at the other of the affiliated facilities;

the second status allows disclosure of the patient information to the second user at the other of the affiliated facilities; and the third status allows disclosure of the patient information to the second user at the other of the affiliated facilities only under a predetermined condition, and the processor of the cloud server automatically approves the viewing request for the second user at the other of the affiliated facilities, under the condition that the flag indicates the second status or under the condition that the flag indicates the third status and the predetermined condition is met, wherein the predetermined condition includes at least one of:
a fact that a target patient had at least one appointment to see a doctor with the other of the affiliated facilities in past, and
a fact that the one of the affiliated facilities permitted the second user at the other of the affiliated facilities to view the patient information.

12. The system according to claim 11, wherein
the examination order information includes first user specific information,
the viewing request includes viewer specific information, and
when determining whether to approve the viewing request, the cloud server determines whether the viewer specific information coincides with or is correlated to the first user specific information.

13. The system according to claim 11, wherein the processor of the cloud server further:
sets a predetermined time limit during which the second user is allowed to view the patient information; and
transmits the setting of the predetermined time limit to the one of the affiliated facilities to allow the second user to view the patient information within the predetermined time limit.

14. The system according to claim 11, wherein the processor of the cloud server further:
receives a filtering request from the one of the affiliated facilities to view one or more pieces of the patient information among the plurality of pieces of the patient information;
searches database in the storage for the one or more pieces of the patient information; and
transmits the one or more pieces of the patient information to the one of the affiliated facilities.

15. The system according to claim 11, wherein the processor of the cloud server further:
correlates disclosure prohibition information to the medical image in the storage, wherein the disclosure prohibition information indicates whether to prohibit the patient information from being disclosed;
determines whether to prohibit the patient information from being disclosed based on the disclosure prohibition information, and
prohibits the patient information from being disclosed regardless of the determination made based on the flag.

* * * * *